(12) United States Patent
Harman

(10) Patent No.: US 8,482,418 B1
(45) Date of Patent: Jul. 9, 2013

(54) METHOD AND APPARATUS FOR MONITORING AND TREATMENT OF SLEEP-RELATED CONDITIONS

(75) Inventor: Polly Harman, Wilmington, NC (US)

(73) Assignee: Pursuit Enterprises

( * ) Notice: Subject to any disclaimer, the term of this patent is extended or adjusted under 35 U.S.C. 154(b) by 0 days.

(21) Appl. No.: 13/563,901

(22) Filed: Aug. 1, 2012

Related U.S. Application Data

(63) Continuation-in-part of application No. 13/400,568, filed on Feb. 20, 2012, now abandoned.

(60) Provisional application No. 61/444,596, filed on Feb. 18, 2011.

(51) Int. Cl.
*G08B 23/00* (2006.01)
*A61B 5/103* (2006.01)
*A61B 5/04* (2006.01)
*A61B 5/00* (2006.01)
*A61B 18/18* (2006.01)
*A62B 7/00* (2006.01)
*A61F 5/56* (2006.01)
*A61N 1/00* (2006.01)

(52) U.S. Cl.
USPC ........ 340/573.1; 340/575; 600/590; 600/587; 600/546; 600/300; 600/391; 128/200.24; 128/848; 607/137; 606/21

(58) Field of Classification Search
USPC .................. 340/573.1, 575, 576; 128/200.24, 128/848, 774, 782, 733; 600/300, 301, 586, 600/590, 595, 391, 528, 509, 546, 587, 559
See application file for complete search history.

(56) References Cited

U.S. PATENT DOCUMENTS

| | | | |
|---|---|---|---|
| 4,644,330 A | 2/1987 | Dowling | |
| 4,715,367 A | 12/1987 | Crossley | |
| 4,788,533 A | 11/1988 | Mequignon | |
| 4,836,219 A | 6/1989 | Hobson et al. | |
| 5,458,105 A | 10/1995 | Taylor et al. | |
| 5,566,067 A | 10/1996 | Hobson et al. | |
| 5,827,198 A * | 10/1998 | Kassal | ......... 600/528 |
| 5,928,133 A | 7/1999 | Halyak | |
| 6,371,120 B1 | 4/2002 | Chiu et al. | |
| 6,544,199 B1 | 4/2003 | Morris | |
| 6,575,902 B1 | 6/2003 | Burton | |
| 7,306,567 B2 | 12/2007 | Loree | |
| 7,559,903 B2 | 7/2009 | Moussavi et al. | |
| 7,639,146 B2 | 12/2009 | Baura | |

(Continued)

OTHER PUBLICATIONS

Vezina, Kenrick; Stick-On electronic Tattoos; Technology Review (MIT), Aug. 11, 2011.

(Continued)

*Primary Examiner* — Jennifer Mehmood
*Assistant Examiner* — Mirza Alam
(74) *Attorney, Agent, or Firm* — Novak Druce Connolly Bove + Quigg LLP; Paul E. Crawford

(57) ABSTRACT

Treatment of sleep conditions is disclosed, particularly snoring, sleep apnea and the related problem of dozing while driving or engaging in activity requiring full attention. Also disclosed are means and methods of pinpointing sleep patterns, particularly therapeutic treatment of sexual disorders. Monitoring of REM sleep cycles to optimize the time for awakening one from sleep is also disclosed.

14 Claims, 7 Drawing Sheets

U.S. PATENT DOCUMENTS

| | | |
|---|---|---|
| 7,716,988 B2 | 5/2010 | Ariav et al. |
| 7,956,756 B2 | 6/2011 | Kubey et al. |
| 8,116,841 B2 * | 2/2012 | Bly et al. ............ 600/391 |
| 8,179,270 B2 | 5/2012 | Rai et al. |
| 2005/0131288 A1 * | 6/2005 | Turner et al. .......... 600/391 |
| 2005/0177051 A1 * | 8/2005 | Almen ................ 600/509 |
| 2009/0312817 A1 * | 12/2009 | Hogle et al. ............ 607/54 |
| 2010/0228315 A1 | 9/2010 | Nielsen |
| 2011/0034912 A1 * | 2/2011 | de Graff et al. ......... 606/21 |

OTHER PUBLICATIONS

Blakely, Lindsay; See the Coolest Sleep Technology at CES, Inc.; Jan. 12, 2012.

Aylesworth, Catherine; ANT—the power of less; Thisisant.com; Jun. 2008.

Dae-Hyeong, Kim et al—Epidermal Electronics; Science; Aug. 12, 2011; vol. 333; p. 838 et seq.

* cited by examiner

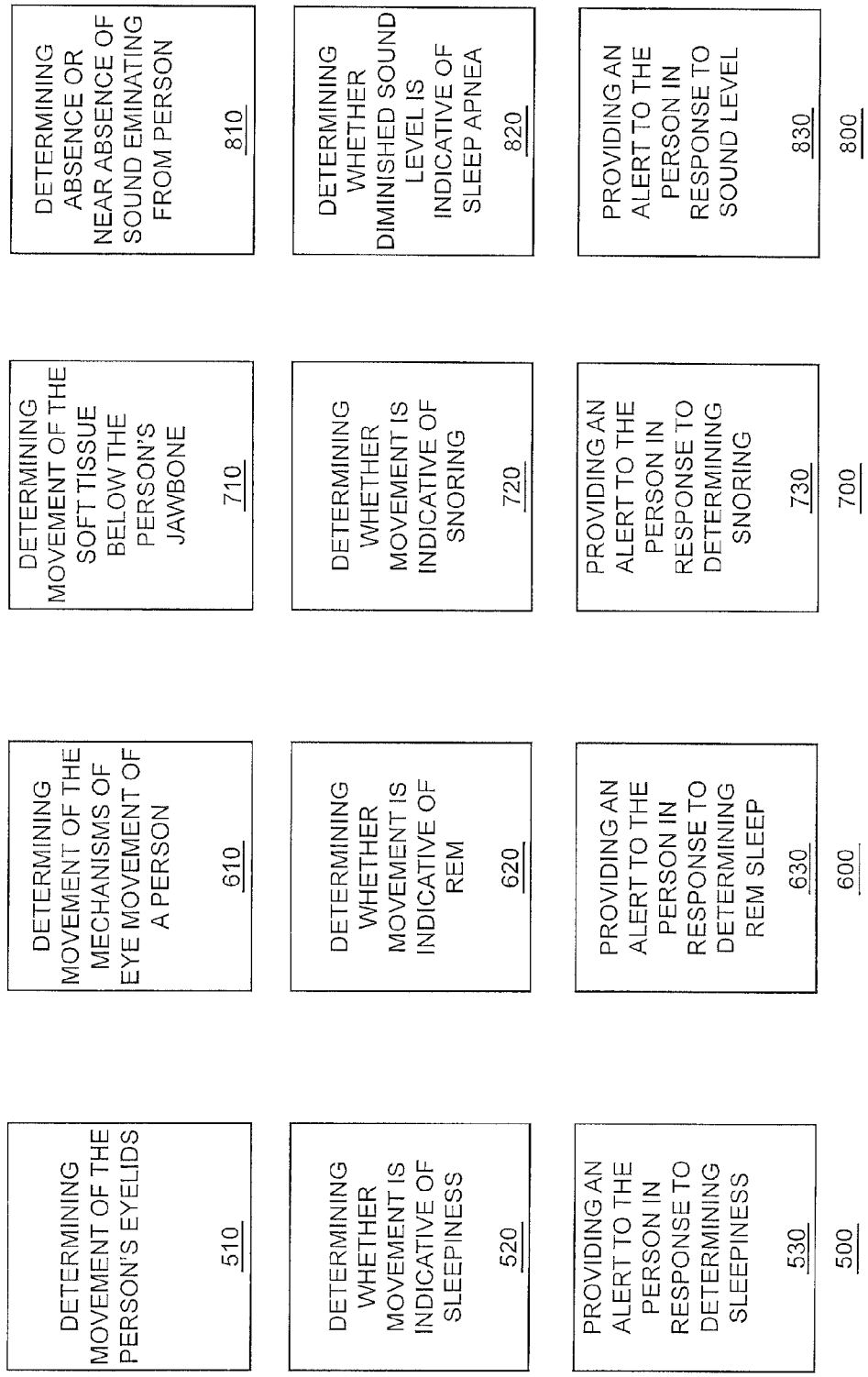

METHOD AND APPARATUS FOR MONITORING AND TREATMENT OF SLEEP-RELATED CONDITIONS

CROSS REFERENCE TO RELATED APPLICATIONS

This application claims priority of U.S. patent application Ser. No. 13/400,568 filed Feb. 20, 2012 entitled "Device for the Treatment of Sleep-Related Conditions" and to U.S. Provisional Patent Application Nos. 61/444,596 filed Feb. 18, 2011 and 61/467,173 filed Mar. 24, 2011.

BACKGROUND OF THE INVENTION

Snoring is common among many humans. During snoring, a sound is produced while breathing during sleep. Snoring may be caused by the vibration of the soft palate and uvula, and, if left untreated, may lead to sleep apnea in which a person can experience abnormally shallow breathing or pauses in breathing during sleep. Sleep apnea can lead to daytime sleepiness, fatigue, trouble concentrating, and other undesirable side effects.

Furthermore, snoring is a nuisance for persons sharing a bed or room with the snorer. One person's snoring may cause the other person sharing a room to also experience uncomfortable or restless sleep and sleep deprivation.

Snoring is caused by obstructed air movement while breathing. This is usually due to a blockage of the breathing passage, which is often due to the person's tongue falling back into their throat while sleeping on their back. Accordingly, one manner to treat snoring is to condition the person to sleep on their side or stomach. Until now, it has proven difficult to train persons to sleep in a certain position.

Efforts have been made to develop a device or manner of alleviating snoring and sleep apnea. However, these efforts have resulted in devices which were ineffective, aesthetically or orthopedically unpleasing, or uncomfortable for the person to wear. For example, the conventional treatment device for obstructive sleep apnea is a cumbersome mask called a Continuous Positive Airway Pressure (CPAP) device that has to be strapped to the sleeper's face while sleeping. Furthermore, these efforts are not aimed at training the person to sleep in a position in which snoring and sleep apnea are unlikely to occur. Accordingly, a need remains for a device and/or method that is effective in training a person to sleep in a position in which the person is not likely to snore or to suffer from sleep apnea, a device that is aesthetically pleasing, and a device that is comfortable for the person to wear.

In addition to treating snoring/apnea problems efforts have been made to develop a device that can monitor a person's sleeping patterns, particularly the occurrence of rapid eye movement (REM) associated with REM sleep. REM sleep is a stage of sleep that is characterized by rapid movement of the eyes. Total REM sleep for an adult in a typical 6-8 hour sleep session may consist of 90-120 minutes. Normally REM sleep first occurs about 90 minutes after sleep onset. The first REM period typically lasts 5-10 minutes, with each recurring REM state lengthening. The final REM stage may last up to an hour. REM sleep is characterized by phasic bursts of right or left movement of the eyeball. Phasic bursts are unusual movement at high speed. Normal eyeball movement during sleep is rather slow and lazy. By contrast, REM is intense with both eyeballs moving the same direction in tandem. Because of the rapidity of the eye movement under closed eyelids, detection of REM in a non-clinical setting has been difficult, however, one or more devices and methods disclosed herein are appropriate for meeting this challenge.

Detection of REM sleep and means to awaken persons during REM sleep cycles have potential quality of life and psychological benefits. It has been established that female and male sexual dysfunction can be ameliorated if the affected person is wakened during REM sleep. It has been clinically proven that those persons whose sexual dysfunction is primarily psychological, versus physical, often experience engorgement of sexual organs during REM sleep. Thus, a means to gently awaken such persons during REM sleep can provide a significant enhancement of treatment for sexual dysfunction.

These and other sleep-related conditions are widely prevalent with some estimates that there are 50 million habitual snorers in the United States. Amelioration of such conditions has been addressed in various patents and published applications discussed below. However, despite the plethora of devices described in these patents, few, if any, have proven to be commercially viable, largely because they are cumbersome and/or unduly interfere with the normal sleep process.

Another sleep-related condition is unwanted dozing while driving, or in other circumstances, where sleep is unwanted. While most prevalent in the context of long-haul trucking, any driver is a potential candidate to lose control of a vehicle by dozing while driving. A person monitoring a dangerous manufacturing process, standing watch in military combat, in a training environment or air traffic control are other situations where dozing could be dangerous. Thus, there is a substantial need for an effective remedy to limit the human carnage and property loss resulting from persons falling asleep where full attention is required. Despite this need, effective means to alert someone when he or she is in the process of falling asleep have not surfaced, largely because of cumbersome and unsightly anti-dozing devices developed to date.

Examples of previously patented approaches to addressing sleep disorders and conditions are discussed below.

Crossley U.S. Pat. No. 4,715,367 attempts to treat multiple sleep disorders, including sleep apnea and snoring, with a device that awakens the user with shock treatments when snoring or apnea is sensed.

Hobson et al U.S. Pat. Nos. 4,836,219 and 5,566,067 describe sensors attached to an eyelid of the user to detect sleep patterns. Signals from the sensors are fed by a wire to head gear containing apparatus to analyze the signals and sort them into sleep states, for example, wake, REM and non-REM (NREM). The '067 patent describes one system where a sensor, preferably piezoelectric, is attached to an eyelid to detect its movement. When that movement of the eyelid falls below a certain level it activates an audible alarm that alerts the user that he or she is dangerously dozing. This anti-dozing device was developed under a NIH grant for use as a safety system to prevent accidents caused by persons falling asleep while driving (column 1, lines 1-25 of the '067 patent).

Another apparatus and system for monitoring sleep related problems is Halyak U.S. Pat. No. 5,928,133. In this patent the sensor used is a transcutaneous, electrical nerve stimulation ("TENS") electrode attached to a body's extremity (arm, leg) that senses physiological changes in the body corresponding to various sleep periods. The signals generated by the TENS electrodes are analyzed and when optimum signals are sensed a buzzer sounds to awaken persons from sleep during the optimal (for that person) wake-up time.

Multiple patents disclose devices which respond to the sound of snoring that, in turn, activate alarms, both auditory and vibratory, to wake up a snoring person. Such patents include U.S. Pat. Nos. 4,644,330; 4,788,533; 5,458,105 and 6,544,199. The latter also discloses an unspecified sensor for measuring "changes in a muscle group" that is related to snoring. To date the acceptance of these patented anti-snoring devices has been very low to negligible because, inter alia, the alarms on the devices also wake up anyone else in the room and the sensors are inaccurate. In a similar vein U.S. Pat. No. 7,716,988 discloses a wrist mounted sensor to detect snoring of one or more persons which activates a vibratory device to awaken the snorer—and usually others in the same bed.

Patents attempting to identify particular sleep patterns have also issued. Loree U.S. Pat. No. 7,306,567 discloses an accelerometer strapped to a limb that monitors movement of that limb. That movement can be an indicator that the person is in a shallow sleep cycle when it is generally better to awaken a person from sleep. The accelerometer is linked to trigger an alarm, audible or visual, when the person is in the desired shallow sleep cycle.

A sleep apnea detector is disclosed in Moussavi et al. U.S. Pat. No. 7,559,903. According to this patent an accurate diagnosis of apnea is difficult and expensive because symptoms are many and varied requiring several sensors recording multiple bodily functions. This patent describes a system where three sensors (two on the sleeping person and one recording background noise) allegedly provides sufficient data to diagnose sleep apnea.

SUMMARY OF INVENTION

This Summary is provided to introduce a selection of concepts in a simplified form that are further described below in the Detailed Description of The Invention. This Summary is not intended to limit the scope of the claimed subject matter.

Disclosed herein is a new, unobtrusive but highly effective system used for medical, commercial, and consumer applications that includes a sensor that is linked to an alert indicator or alarm preferably located near or in an ear of a person for providing alerts to the person. The alert indicator is preferably deformable for conforming with, and easy insertion into, the ear canal of the person. According to one embodiment, the alert indicator emits an audible alarm, although vibratory alerts are also contemplated.

The alert indicator or alarm is configured to provide alerts when a sensor attached to a person senses a condition that warrants activation of the alert. The alert indicator/alarm, for example, can emit an intermittent audible alert when the sensor senses that the person is snoring. The alert preferably contains a miniaturized speaker or other noise generator at its inner portion (facing the eardrum). This directs the alarm sound to the eardrum and away from anyone sleeping nearby who might be awakened or bothered by the alarm noise.

The sensor described herein utilizes new, unique technology which enables monitoring of different bodily functions and parts so that the same type of sensor can be used to identify multiple sleep-related conditions, for example, apnea, snoring, dozing, and REM sleep. Identifying REM periods of sleep is important in treating psychological sexual dysfunction and to optimize or pinpoint the ideal waking moment in REM sleep for mental clarity and function.

This monitoring approach is new and different in that all components of the sensor used to measure bodily functions associated with these sleep conditions can be mounted onto an ultra-thin, small, low-modulus, lightweight, gas permeable, stretchable, "skin-like" membrane that comfortably laminates onto the surface of a person's skin much like a temporary "tattoo." The sensor contains multiple electrical components arranged on the membrane that monitor, analyze and send a signal to an alarm for it to activate in response to the varied sleep conditions being monitored.

This sensor is preferably used on the user but may be implanted into the person's skin. This sensor is preferably configured for detecting movement of underlying muscles associated with some or all of the sleep-related conditions discussed herein.

In one embodiment a sensor is applied to a person's face adjacent that person's eye to detect the operation of muscles that control eye movement. The sensor may be placed adjacent the person's eye, eyelid, or tissue or muscle about the orbital bone. In this manner, the sensor may be configured for detecting movement of the eye by monitoring the electrical impulses emitted by muscles near or attached to the eye. The sensor of this invention is particularly sensitive and is able to monitor the electrical potential generated by muscle cells, including the muscles that (1) control the movement of the eyeball for detecting REM; and (2) muscles that control eyelid movement, for detecting dozing.

In one or more embodiments, such a sensor, utilized in conjunction with an alert indicator, may be used to detect and predict the onset of dozing, such as, for example, while driving or performing other tasks. In this manner, one aspect of applicant's system may call for an alert device that alerts a user that they are becoming drowsy. The sensor may also be configured for detecting up and down movement of the eyelids. This movement may be indicative of sleepiness or drowsiness. The sensor is preferably connected wirelessly to an alert that may be audible, visual, motion (vibrations) or combinations thereof. A hard wired-connection between sensor and alert is also contemplated.

According to another embodiment, the sensor is configured for sensing snoring by sensing vibrations and their corresponding frequencies of the soft tissue of the person being monitored, particularly at locations below the person's ear and under the person's jaw bone.

In a further embodiment of the invention, a microphone built into the sensor will detect the absence of noise associated with sleep apnea. When detecting sleep apnea the microphone would act like a stethoscope to gather sound, or lack of sound, emanating from the trachea of the sleeping person. When the signal from the microphone in the sensor hears no, or low, noise it triggers the alarm in the sleeper's ear or in an audible alarm in proximity to the sleeper to awaken that person out of an apneic event to restore normal breathing.

It is a further object of this invention to provide one type of sensor useable to monitor and treat all of the major sleep disorders and other conditions noted above, namely, sleep apnea, snoring, dozing, and detection of REM sleep.

This "universal" sensor is characterized by use of stretchable, ultrathin membranes with electronics arrayed thereon that can detect electrical activity from the body such as signals produced by muscle activity underlying the skin, sound emanating from the mouth, as well as physical movement of skin to which it is attached. In this ultrathin sensor, made possible through nano technology, the detection of bodily activity, the power supply to run the electronics and these electronic components are configured together into an ultrathin, lightweight, stretchable "skin-like" membrane that can be applied to the human skin. The sensor is preferably less than four square inches in size and about 50-300 microns in thickness, this ultrathin sensor can be produced in flesh tones that match skin tones of a user thereby making the sensor an aesthetically acceptable addition to the body of the user.

This relative transparency of the sensor makes its use much more acceptable to users than bulky, obvious sensors used in the prior art, for example, the headgear described and disclosed in Hobson U.S. Pat. No. 4,836,219 and the medieval shock treatment approaches disclosed in Crossley U.S. Pat. No. 4,715,367. This relative transparency overcomes reluctance to use bulky, visually apparent prior art devices when appearing in public. Providing a sensor that is inconspicuous improves acceptance of the claimed sleep monitoring device, a factor particularly important with anti-dozing devices used by truckers. They are reluctant to enter a truck stop with a prominent sensor attached to their body.

This ultrathin sensor can be attached to specific portions of the body which emit symptoms of the particular sleep condition to be treated.

In the embodiment for detecting REM sleep the sensor can be placed on the user's face over the muscles around the eye that control eye movement associated with REM. Those muscles include the medial and lateral rectus muscles which control right and left eye movement.

In the embodiment for monitoring dozing, the muscles being monitored are those which control the eyelid, e.g., the orbicularis oculi and levator palpebrae superioris muscles which are located around the orbital bone of the eye and in the eyelid itself and are responsible for blinking. Determining whether there is movement of the person's eyelids is indicative of sleepiness by comparing the detected movement to a predetermined value, and providing an alert to the person in response to determining movement indicative of sleepiness thereof. The amount and timing of movement of the person's eyelids can be monitored to determine possible dozing.

In the embodiment for monitoring snoring the sensor monitors the movement of the underlying muscles and skin surface adjacent the neck of the person being monitored to detect vibration of those body parts associated with snoring.

In the embodiment for monitoring sleep apnea the sensor utilizes a microphone integrated onto the surface of the sensor to detect the absence of, or diminished amount of, breathing associated with sleep apnea.

The sensor attached to the user's body can be made to contain its own power source and wireless communication components integrated on the surface of the sensor.

Once an actionable condition is sensed by the sensor it activates an audible alert indicator or alarm that stimulates a response from the person being monitored.

According to one embodiment, the alert indicator emits an audible alert. According to another embodiment, the alert indicator is configured to provide alerts when the sensor senses that the person is snoring. According to another embodiment, the alert indicator emits an intermittent audible alert when the sensor senses that the person is snoring. According to another embodiment, the alert indicator emits a constant audible alert when the sensor senses that the person is snoring.

The audible alert indicator is preferably configured for being received in an ear canal of a person and is preferably triggered by a wireless communication from the sensor.

Optionally the alarm can comprise a vibratory device to stimulate a response from the user.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawing exemplary embodiments; however, the presently disclosed invention is not limited to the specific methods and instrumentalities disclosed. In the drawings:

FIG. 7 is a flow chart depicting a method according to one or more embodiments disclosed herein;

FIG. 8 is a flow chart depicting a method according to one or more embodiments disclosed herein;

FIG. 9 is a flow chart depicting a method according to one or more embodiments disclosed herein; and FIG. 10 is a flow chart depicting a method according to one or more embodiments disclosed herein.

DETAILED DESCRIPTION OF THE INVENTION

This description itself is not intended to limit the scope of this patent. The claimed invention might also be embodied in other ways, to include different elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 1:
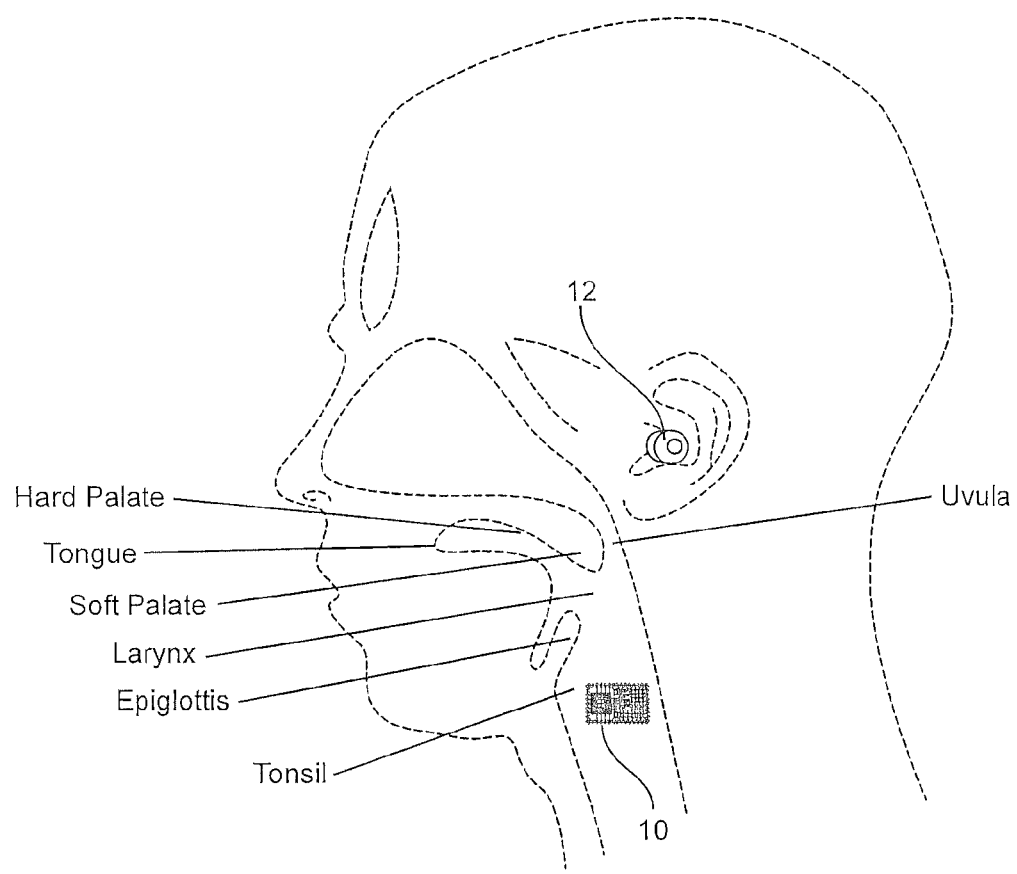
FIG. 1 is a pictorial view of the sensor and alarm of this invention, and further showing anatomical features of the person that may interact with the overall device according to one or more embodiments of the disclosed subject matter.

FIG. 1 illustrates one placement of sensor 10 and alert indicator/alarm 12 on the human anatomy which includes an alert indicator or alarm 12 configured for preferably being received in the ear, although it could also be arranged in proximity to the ear, attached or otherwise engaged with the ear. The alert indicator 12 may be for providing alerts to the person. This embodiment includes a sensor 10 configured for sensing snoring of the person. Wireless communication between sensor and alarm 12 is provided as discussed below.

A preferred sensor 10 for use in applicant's system for monitoring sleep disorders comprises a "skin like" membrane that conforms to the surface of the wearer's skin so it is essentially a second skin that bends, stretches, contracts with the person's skin much like a temporary transfer tattoo. That membrane should be an ultrathin (30-300 microns, preferably 30-50 microns), stretchable material, for example, a modified polyester film which is gas permeable with a low Young's modules. Operational electronic components described below are deposited on the ultrathin membrane and adhere to the user's skin as described below.

The term "ultrathin membrane" as used herein refers to any media on which the described electronic components can be mounted, either temporarily or permanently, and which will readily act to maintain the electronic components of the sensor in place on human skin (by adhesive or van der Waals forces) in a manner that it becomes a second skin, i.e., as the skin goes so goes the membrane and/or the electronic components deposited on the skin. Thus, if the skin wrinkles the membrane and/or electronic components wrinkle with it. If the skin stretches or contracts the membrane and/or electronic components correspondingly stretch and contract. Exemplary ultrathin membranes include thin gas permeable, polyester sheets. Temporary membranes fashioned, for example from polyvinyl alcohol (PVA), can be used to hold electronic components in place before being applied to the skin of the user. Once the PVA containing the electronics is in place, the PVA can be dissolved with water leaving the electronic components operational and in place on the skin.

This sensor can also be colored to match flesh tones of the user. This promotes use of the claimed device by those who previously shunned sleep disorder detectors because their use was so apparent to those who were in contact with the user.

Figure 6:
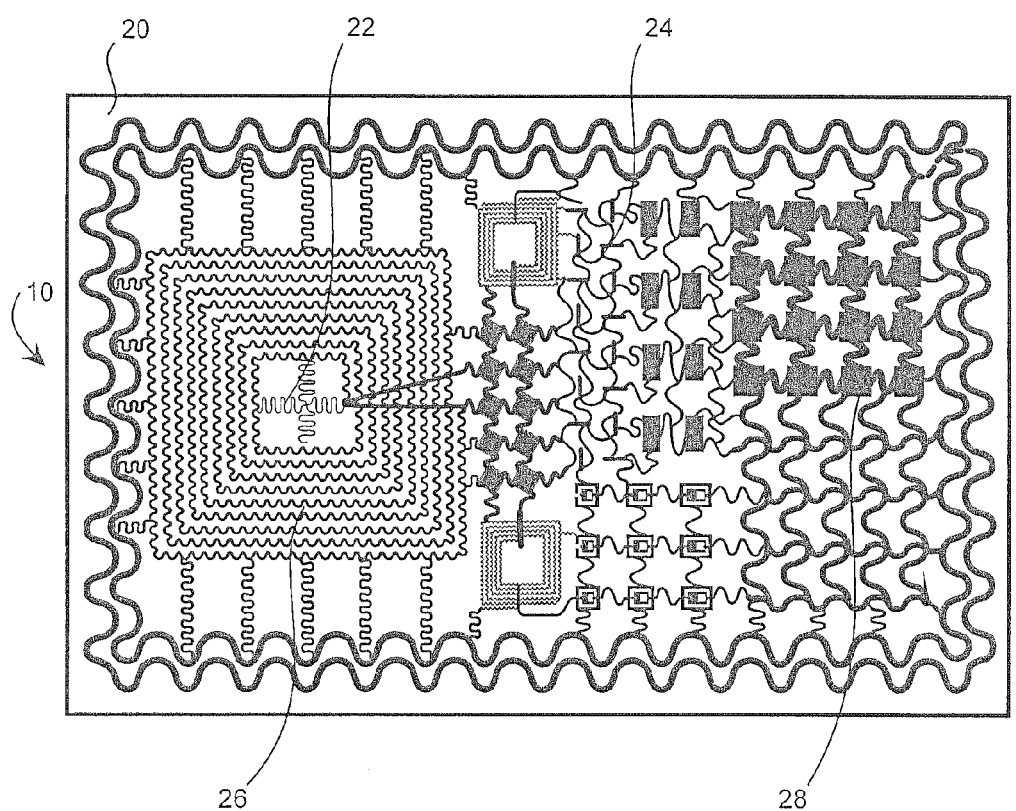
FIG. 6 is a pictorial view of an ultrathin membrane sensor useable in this invention showing various components of the sensor and means for wirelessly communicating sensor outputs therefrom.

Ultrathin membranes of the type just described can be assembled with electronic components mounted thereon, for example, strain gauges, EMG detectors, microphones, power supply, communication components, temperature gauges and the like. FIG. 6 illustrates one embodiment of such an ultrathin membrane 20 with active components for recording and transmitting information. The active components of the sensor such as the antennae 22 (for wireless communication to the alarm), strain gauges 24, power sources 26, EMG sensor 28, microphone and comparator circuits (not shown) for signaling alarm 12, etc. are preferably mounted on the membrane in the form of serpentine ribbons as illustrated in FIG. 6. This serpentine configuration facilitates stretching and contraction of the electronic components to match movement of the underlying skin. The serpentine configuration likewise facilitates loading of more component structure on a small surface area. Power generation for the electronic components can be provided from a new class of power sources based on thermal gradients present on the surface of the skin. Other in situ human power sources include the human heart and pulse of blood vessels. A leading developer of such power sources for use with skin mounted sensors is a company, MC 10 of Cambridge, Mass.

The sensor 10 with electronic components thereon can be applied to the user's skin using suitable adhesives on at least one side of the supporting membrane 20. Alternatively, the sensor can be attached by putting a PVA membrane with electronic components over the user's skin and then washing away the PVA as discussed above. Dissolving the PVA leaves the electronic components attached to the skin through van der Waals forces.

Other forms of sensors useable with this invention include miniature piezoelectric film sensors. Such a sensor may be used as an external sensor such as that which is depicted in one or more Figures disclosed herein, or in one or more embodiments, may be implanted into or on the person's skin.

A sensor 10 of this invention may be configured for detecting movement of the eye or eyelid of a person and is preferably located over or very near the muscles controlling that movement. The sensor 10 can be placed on the neck area of a person at or near the uvula (See FIG. 1) to detect the vibration of throat tissue associated with snoring. A similar location, or one close to the mouth, can be used for placement of sensor 10 with a microphone contained thereon to measure the absence of sound associated with sleep apnea.

The sensor 10 has multiple applications, including detection of Rapid Eye Movement (REM) sleep. In one or more embodiments, such a sensor 10 utilized in conjunction with alert indicator 12 may be used to detect and predict the onset of dozing, such as, for example, while driving or performing other tasks. In this manner, one aspect of the device may call for an alert device that alerts a user that they may becoming drowsy. Sensor 10 may also be configured for detecting up and down movement of the eyelids. This movement may be indicative of sleepiness or drowsiness. In this manner, alert indicator 12 may be configured for providing an alert if it is determined that the person is sleepy or drowsy.

Figure 5:
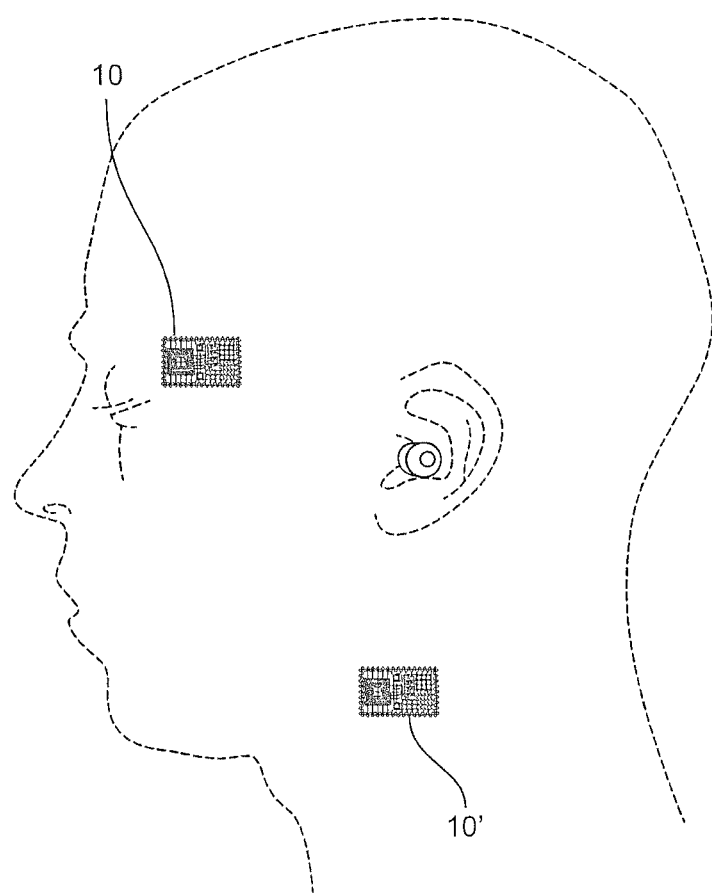
FIG. 5 is a pictorial view of a device for use according to one or more embodiments wherein sensors adjacent the throat area and eye of a user are used in tandem to monitor sleep-related conditions of the user.

Multiple sensors according to an alternate embodiment are shown in FIG. 5 and depicted as 10 and $10^1$. Sensor 10 may be positioned proximal a person's eye, to sense movement of the eye or eyelid of the person. Each of the sensors 10 and $10^1$ may be in communication with one another and an alarm. Sensors 10 and $10^1$ may work together to monitor one or more conditions of the person with sensor $10^1$ monitoring breathing. Further processing of the monitored conditions by multiple sensors may provide additional data that may be indicative of a medical or non-medical state of the person.

Any sensor used in this invention preferably has the primary characteristics of the above-described sensors, namely, it should be able to be placed so as to detect even minor movement of human tissue, skin or underlying muscle associated with the condition being monitored. For dozing detection this would be movement of muscles controlling eyelids. For REM this would be detection of rapid eyeball movement. Both the eyelid and eye movement are controlled by muscles connected to the eye. Placement of a finger adjacent the eye when the eyeball and/or eyelid is in motion provides testimony to the role of these muscles in eye and eyelid movement.

There are multiple muscles that control blinking, the degree of which can be used to determine dozing. The main muscles in the upper eyelid that control the opening and closing of eyelids associated with blinking are the orbicularis oculi and levator palpebrae superioris muscles. The orbicularis oculi closes the eye, while the relaxation and contraction of the levator palpebrae muscle opens the eye. These muscles are readily sensed on the surface of the face by placing a sensor in the area adjacent the side of the eye. The preferred location of the sensor for detecting eyelid movement can be determined by simply placing a finger in or around the side of the eye socket and the eyelids. The muscles responsible for the blinking can be readily felt under the finger. The sensor 10 is then placed over the area where these muscles were felt.

The average length of a blink is 100-400 milliseconds (ms). Closures in excess of 100 ms are defined as microsleeps. Normal blink rate is 10 per minute. Sensor 10 placed adjacent the eye can detect eye movement outside this range which indicates dozing. When dozing is detected it sends a signal to the alarm 12 to alert the person that he/she is dozing.

Figure 4:
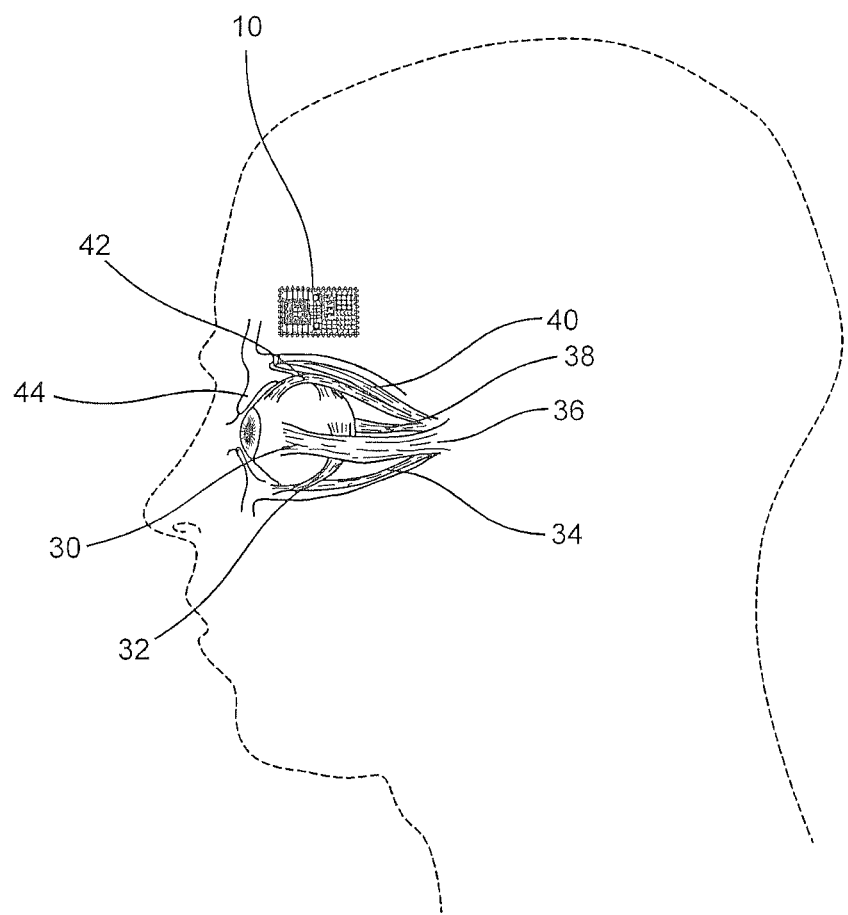
FIG. 4 is a pictorial view of the sensor located adjacent the muscles that control eye movement.

For REM detection the sensor 10 is placed to monitor the muscles and nerves controlling left and right movement of the eye. Proper functioning of the eye requires six muscles that control movement. They work together to offer a wide field of vision and movement, allowing for up, down, left and right movements. The eye is housed in the orbit of the skull and the six muscles hold it suspended in place as illustrated in FIG. 4.

The muscles responsible for left and right eye movement related to REM conditions are the lateral rectus 36 and medial rectus 38. Other muscles controlling eye movement up and down are the inferior rectus 34 and superior oblique 40.

The eye muscles work in pairs and movement of the eye muscle is often only a very small movement, a fraction of a degree. The muscles need to be coordinated for vision to be stereoscopic (three-dimensional vision). For example, if you look to the left, the lateral rectus muscle on the left side of your left eye contracts. At the same time, on the right side of the same eye, the medial rectus relaxes.

Even though the muscles controlling left and right eye movement do not move a lot their movement is sufficient to be sensed for providing a signal indicative of REM sleep. The sensor 10 is placed over or adjacent these muscles. The EMG component of sensor 10 is sensitive enough to sense movement of the abovementioned muscles which control right and left movement of the eye symptomatic of REM sleep. Placement of the sensor 10 over these muscles is facilitated similarly as with placement described above with the muscles controlling eyelid movement. They can be felt by placing a finger near the side of the eye and moving the eyeball to left and right in a manner (albeit slower) than that which occurs in REM sleep.

Once these conditions are sensed and found to be indicative of these conditions a signal is sent from the sensor 10 to the alarm 12 to awaken that person being monitored.

For snoring, sensor 10 detects vibratory movement of the soft tissue below the ear and under the jawbone of the person. See FIGS. 1 and 2. In this manner, the sensor 10 will be positioned in relation to soft tissue that is interconnected with, and in proximity to, the epiglottis, tonsils, uvula, and larynx as illustrated in FIG. 1. During snoring caused by, for example, the person's tongue falling back into the person's throat while the person is sleeping on their back, air flow through obstructed trachea or air passage would cause a vibration about the soft tissue. The sensor 10 may be configured to sense this vibration of the soft tissue. According to embodiments of the present invention, the sensor 10 may be configured to sense any suitable characteristics in addition to vibrations. For example, the sensor 10 may be configured to additionally detect sounds associated with breathing using a microphone.

For sleep apnea the sensor 10 may be configured to detect breathing, the absence of breathing or the presence of abnormally shallow breathing, or all of these conditions. The sensor 10 may detect the absence of breathing or shallow breathing via a microphone in sensor 10 that would sense the absence, or near absence, of sound associated with breathing.

Detection of the REM portion of a sleep pattern has at least two important clinical functions. First, the REM portion of sleep is the point in the overall sleep cycle where the depth of sleep is the shallowest. Therefore it is the point in the sleep pattern at which the human body is best able to wake-up with the least sleep residual. Second, during REM sleep the sexual organs of both male and female are typically engorged with blood. Thus, for those with psychological sexual dysfunction, awakening from REM sleep provides the greatest potential for successful sexual intercourse. The sensor-alarm of this invention can detect the eye movements associated with REM sleep and activate the alarm at the right time to enhance treatment of sexual dysfunction and optimize the ideal waking moment in REM sleep for mental clarity and function.

In accordance with one or more embodiments, sensor 10 may be in communication with an external computer device (not shown) that contains appropriately configured computer programmable code and a processor and/or memory for storing and executing the computer programmable code. The computer programmable code may be provided for controlling the sensor 10 or other components of the overall system. The sensor may also transmit via Wi-Fi to a central computer, server or "cloud" environment which can analyze data transmitted by the sensor 10 and, based on that analysis, activate alert 12.

Figure 2:
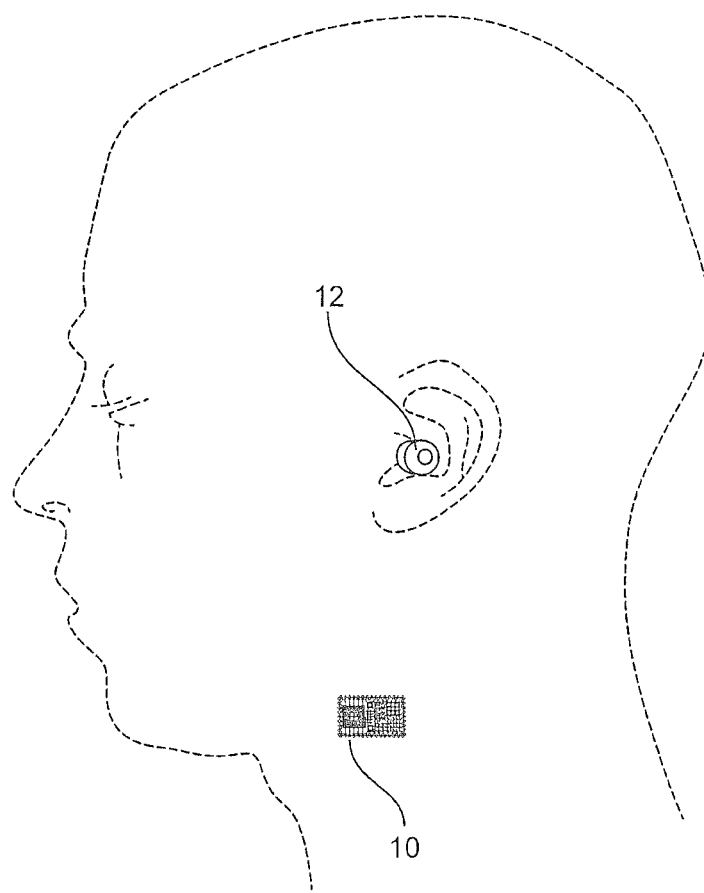
FIG. 2 is pictorial view of the sensor and alarm installed about a person according to one or more embodiments of the disclosed subject matter.
Figure 3:
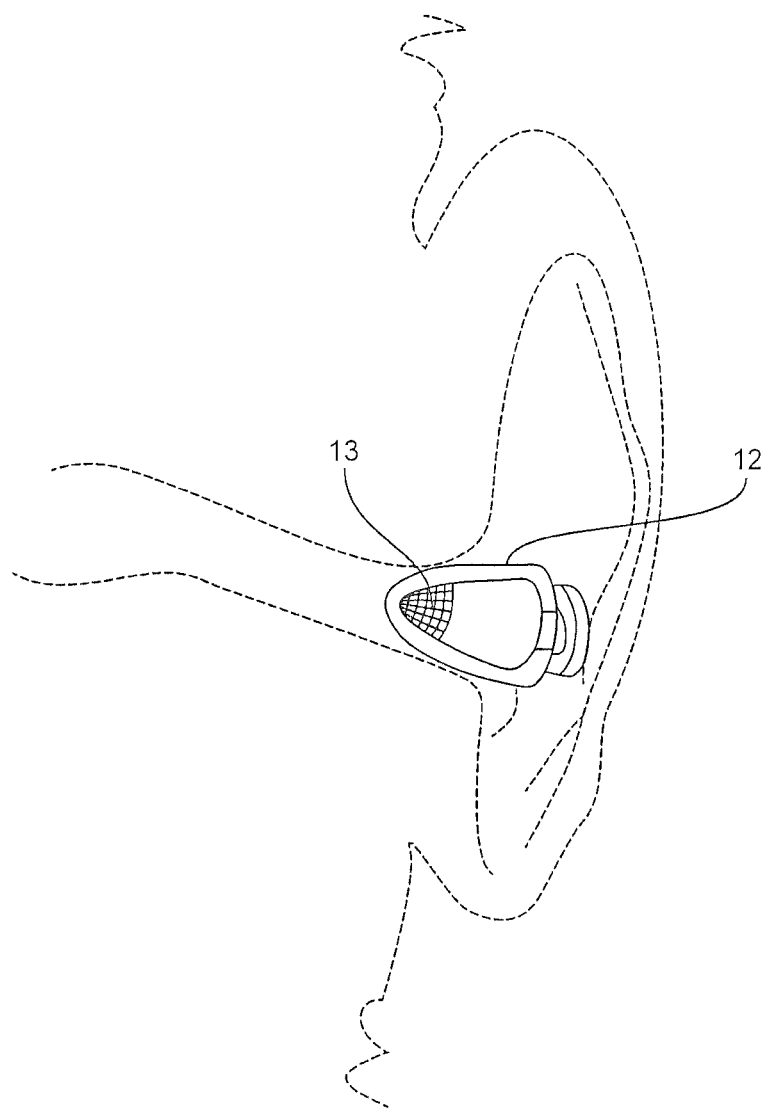
FIG. 3 is a perspective view of the alarm of this invention contained within the ear (shown in broken lines)

The sensor(s) 10 just described are but one part of the overall claimed system. The other component is the alert indicator or alarm 12. The alarm is preferably positioned in the outer ear canal of the system user as illustrated in FIGS. 1-3, particularly FIG. 3. The alarm 12 is further configured to emit an audible alert when the sensor 10 senses snoring of the person. The audible alert may be a high or low pitch sound of varying frequencies. Additionally, the alarm 12 may emit an intermittent audible alert when the sensor 10 senses snoring of the person being monitored, or may emit a constant audible alert when the sensor 10 senses snoring of the person. The alarm 12 may also provide audible alerts that are recognizable to persons other than the person, or may provide audible alerts that are only to be heard by the person.

In one or more embodiments described herein, the audible alerts are emitted in the direction of the person's ear canal and are of a volume intensity such that only the person can hear the audible alert. A portion of the alarm 13 directed toward the ear canal (See FIG. 3) is preferably comprised of an open mesh to facilitate the transmission of sound from the alarm 12 to the user's ear drum. In this manner, a person sharing a bed with the person would not be bothered by the audible alert. The alert indicator 12 may take on many varying shapes and sizes, and may be provided with deformable characteristics so as to deform to fit comfortably within the person's ear canal.

The alarm 12 could also be positioned so it could be heard or sensed by others to facilitate a reaction to, or recording of, the signal sent by sensor 10. In a clinical setting sensor output might be recorded as part of a sleep study without waking the person whose sleep habits is being studied. Or children susceptible to Sudden Infant Death Syndrome (SIDS) might wear sensor 10 which transmits to a remote alert where the parent or guardian is sleeping.

Communication between the sensor 10 and alert indicator/alarm 12 is preferably wireless, although wired communication between these components is also an option, particularly in the clinical settings described above. In clinical settings the need for miniaturization and concealment of the device components is not as important to the user as, for example, dozing detection on a truck driver entering a truck stop or snoring detection on an amorous couple going to bed. The wireless communication between the sensor and alert indicator is achieved using a miniaturized RF transmitter whose components (such as capacitors, oscillators and antennal) are integrated onto the ultrathin membrane 20 discussed above. One embodiment of such transmitter and other (strain gauge, antennae, etc.) components of an ultrathin sensor is disclosed in an article entitled "Epidermal Electronics" by Dae-Hyeong Kim et al, published in Science, Vol. 333, pages 838, et seq (2011) available at www.sciencemag.org/content/333/6044/838.full.html. This article is fully incorporated by reference herein. A more detailed description of such a sensor is set forth below and in FIG. 6.

A preferred sensor embodiment of this invention is typically less than four inches square and less than 300 microns thick, yet durable and stretchable. The base structure or membrane 20 of this sensor 10 is a stretchable gas permeable sheet, for example a modified polyester as mentioned above. As previously noted, this sheet can be adhered to the user's skin using adhesives or using a water soluble substrate like PVA that can be washed away, not unlike a temporary transfer tattoo.

The sensor 10 is durable enough that it can be worn for a period of 24 hours or more without degradation before it needs to be replaced. When it needs to be removed it can be peeled off by the user by simply lifting a corner of the sensor and pulling. In the case of the sensor formed on water soluble PVA, the electronic components deposited on the skin after washing away the PVA can be easily washed or scraped off the skin because they only adhere to the skin with van der Waals forces.

One function of sensor 10 is to monitor the movement of the user's muscles under the skin as noted above. Underlying muscle tissue movement is detected by electromyograms (EMGs) on the sensor 10 capable of measuring such movement. The sensor can also be made with strain gauges mounted thereon that use electrically conductive silicon (CP-DMS) to monitor skin movement, e.g., when monitoring snoring. A microphone (not shown) can be incorporated in sensor 10 when used to monitor conditions indicative of sleep apnea.

The flowchart of FIG. 7 illustrates general steps of monitoring a person to determine one or more conditions thereof. The method 500 includes detecting movement of the person's eyelids (step 510) by monitoring the muscles controlling the eyelids. This detection may employ any of the sensors disclosed herein.

The method of utilizing sensor 10 and alarm 12 for treatment of sleep disorders is examined below. Typical placement of sensor 10 for detecting dozing is near the person's eye socket as generally illustrated in FIG. 4. In FIG. 4 sensor 10, for illustrative purposes, is located above the eye. Its actual placement for detecting dozing will be lower on the face directly over the muscles used to control eye blinking as discussed above. A comparator circuit on the sensor (not shown) is preprogrammed to sense "normal" movement of the eyelid or eye versus abnormal movement indicative of dozing (step 520 of FIG. 7). When abnormal movement is sensed the sensor emits a signal over the antenna 26 (FIG. 6) which triggers the alert 12 to emit sound, vibrate or otherwise alert the user (step 530 of FIG. 7).

The signals from sensor 10 will distinguish between normal blinking rates and rates associated with dozing. Most people will involuntarily blink their eyes with some predetermined frequency, typically about 10 times per minute. When, and if, the frequency of blinking is reduced below a normal level this is sensed by the electronics built into the sensor. If that condition is sensed a wireless signal is then sent from the sensor to the alarm 12 to activate it. Once activated, the alarm 12 emits an audible or vibratory output that is of sufficient magnitude to alert the user that he or she is dozing.

Thus, when a sensor 10 senses that the muscles indicating opening and closing of eyelids have slowed or stopped (step 520 of method 500) it sends a signal to the alarm 12 to awaken the person (step 530 of method 500). Alternatively the sensor signal may be transmitted to a remote device, e.g., central offices for monitoring trucks, airlines, and military operation, for action and intervention.

A similar method is illustrated in the flowchart of FIG. 8 in which a method 600 is provided. The method 600 may include detecting the mechanisms of eye movement of a person (step 610). This detection may employ any of the sensors 10 disclosed herein. The sensors may be configured for detecting movement of the person's eyes—as opposed to the eyelids—similar to that which is described with reference to one or more methods of FIG. 7. For example, this detection may be made by determining whether the movement of the eyeball is within a predetermined value associated with the condition that is being examined or alternatively outside a predetermined value that is associated with that or some other condition. The sensors may be positioned at each of the person's eyes, or just one of the person's eyes.

To sense eye—versus eyelid—movement the sensor 10 is preferably located adjacent one or both eyes on the face immediately adjacent the eye. In this position the sensor 10 can sense the underlying muscles that control movement of the eye, particularly while a person being monitored is asleep. REM sleep is characterized by phasic bursts of rapid eye movement of detroversion and levoversion, or right and left. This particular eye movement occurs only during REM sleep. These phasic or frantic bursts have been seen during polysomnography at a rate of 1 or more per 30 second epoch of recorded data. That movement, of necessity, implicates movement of muscles that control movement of the eye. The sensor 10 can be configured to detect quick, rapid movement of such muscles characteristic of REM sleep as indicated in step 620 of FIG. 8. When such movement is detected a signal is transmitted from the sensor to the alert 12 to awaken the person as indicated in step 630 of FIG. 8. The signal can be delayed to a period of REM sleep late in the overall sleep period of 6-8 hours so that sleep is not prematurely interrupted.

This alert and consequent awakening can be used to promote sexual activity as discussed above. Moreover, because the REM sleep period is also the time when the person awakened is most alert it is an optimal period during the overall sleep cycle to awaken and face the day.

The flowchart 700 in FIG. 9 illustrates general steps of monitoring a person to determine one or more conditions, particularly snoring. This method includes detecting movement of the soft tissue in the person's neck, below the jawbone, as indicated in step 710. This detection may employ any of the sensors disclosed herein. The sensors may include an accelerometer, a piezoelectric sensor, strain gauge or like devices that can adequately detect movement of soft tissue associated with snoring. As an addition, or alternative to, detection of soft tissue movement, sensor 10 may also include systems and circuitry to detect sounds associated with snoring. The alert may be sounded so the person being monitored awakes and shifts into a non-snoring position or transmitted to a remote location for monitoring.

This repeated awakening can be used to train a person to sleep with the correct position so as to eliminate snoring. For example, if a person is sleeping in a position in which they begin to snore, sensor 10 senses that state of snoring and alert indicator 12 then provides alerts to the person. As a non-limiting example thereof, the alert may be an audible signal. In this manner, the alert indicator 12 continues to emit an audible signal until the sensor 10 no longer senses snoring. This could be because the person has repositioned themselves in a sleeping position in which the person's airways are not restricted and therefore there is no snoring. Accordingly, the person will learn to sleep in a position in which they are not likely to snore.

Methods for detecting sleep apnea of a person are disclosed in flowchart 800 of FIG. 10. The method may generally include detecting the absence, or near absence, of breathing by a person, and providing an alert to the person in response to absence of breathing. That alert could be on or near the person being monitored for apnea or transmitted to a sleep disorder clinic or location of a caregiver or doctor.

In one or more embodiments, the sensors disclosed herein may be configured for monitoring more than one characteristic. For example, sensor 10 may be further configured for monitoring a characteristic such as sound, electrical charges from contracting and expanding muscles, perspiration, and the like. In this manner, for example, sensor 10 may be configured for both detecting vibration or other movement of the soft tissue below the person's jawbone and for detecting, for example, sound emanating from the person. The sensor 10 may then compare on or more attributes of the additional characteristic to the detected vibration. For example, if the sensors sense movement of the soft tissue of a certain amplitude and frequency, and also senses a sound of a similar amplitude and frequency, this may further verify that snoring has been detected.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

The invention claimed is:

1. A system for monitoring snoring, REM, sleep apnea or dozing of a sleeping person comprising a universal sensor sensing the movement of subcutaneous muscles during periods of REM and an alert indicator wherein
the universal sensor comprises
an ultrathin, flexible membrane adhered to the sleeping person's skin above and adjacent to that person's subcutaneous muscles that control eye movement associated with rapid eye movement;
electronic components mounted on the membrane, configured to sense movement of the subcutaneous muscles during periods of rapid eye movement and
electronic transmission media mounted on the membrane for wirelessly transmitting information sensed by the universal sensor;
the alert indicator comprises a receiver of the information transmitted by the universal sensor, and a signal emitter configured to emit an audible or vibratory signal when the information transmitted by the universal sensor indicates the sleeping person is experiencing a period of rapid eye movement.

2. The system of claim 1 wherein the ultrathin membrane comprises a gas permeable, stretchable material having the thickness of less than about 300 microns and a total area of up to about 4 square inches which is used to hold the electronic components in place when they are applied to the skin of the user.

3. The system of claim 1 wherein the subcutaneous muscles being monitored are those controlling left and right movement of the person's eyeball.

4. The system of claim 3 wherein one or more of the following muscles are monitored: lateral rectus and medial rectus.

5. A system for monitoring snoring, REM, sleep apnea or dozing of a person comprising a universal sensor sensing the movement of subcutaneous muscles during periods of dozing and an alert indicator wherein
the universal sensor comprises
an ultrathin, flexible membrane adhered to the person's skin above and adjacent to that person's subcutaneous muscles that control vertical movement of the person's eyelids
electronic components mounted on the membrane configured to sense movement of the subcutaneous muscles during periods of dozing; and
electronic transmission media mounted on the membrane for wirelessly transmitting information sensed by the universal sensor;
the alert indicator comprises a receiver of the information transmitted by the universal sensor, and a signal emitter configured to emit an audible or vibratory signal when information transmitted by the universal sensor indicates the person is dozing.

6. The system of claim 5 wherein the ultrathin membrane comprises a gas permeable, stretchable material having the thickness of less than about 300 microns and a total area of up to about 4 square inches which is used to hold the electronic components in place when they are applied to the skin of the user.

7. The system of claim 5 wherein the universal sensor is mounted adjacent the side of one or more of the person's eyes.

8. The system of claim 7 wherein movement of one or more of the following muscles is sensed: the orbicularis oculi or levator palpebrae superioris.

9. A system for monitoring sleep apnea, snoring, REM or dozing experienced by a sleeping person comprising a universal sensor detecting the absence of sound associated with a cessation of breathing indicative of sleep apnea and an alert indicator wherein
the universal sensor comprises
an ultrathin, flexible membrane adhered to the person's skin in proximity to the sleeping person's trachea;
electronic components for detecting the absence of sound associated with a cessation of breathing indicative of sleep apnea mounted on the membrane, and
electronic transmission media for wirelessly transmitting information sensed by the universal sensor;
the alert indicator comprises a receiver of the information transmitted by the universal sensor, and a signal emitter configured to emit an audible or vibratory signal when the information transmitted by the universal sensor indicates the person is experiencing sleep apnea.

10. The system of claim 9 wherein the ultrathin membrane comprises a gas permeable, stretchable material having the thickness of less than about 300 microns and a total area of up to about 4 square inches which is used to hold the electronic components in place when they are applied to the skin of the user.

11. The system of claim 9 wherein the membrane has mounted thereon electronic components capable of detecting the absence of sound associated with sleep apnea.

12. A system for monitoring snoring, REM, sleep apnea or dozing by a sleeping person comprising a universal sensor detecting vibration of the neck tissue indicative of snoring and alert indicator wherein
the universal sensor comprises
an ultrathin, flexible membrane adhered to the sleeping person's neck tissue in close proximity to the sleeping person's vibrating soft tissue located below the person's ear and under the jawbone;
electronic components for detecting vibration of the neck tissue indicative of snoring mounted on the membrane, and
electronic transmission media for wirelessly transmitting information sensed by the universal sensor;
the alert indicator comprises a receiver of the information transmitted by the universal sensor, and a signal emitter configured to emit an audible or vibratory signal when the information transmitted by the universal sensor indicates the person is snoring.

13. The system of claim 12 wherein the ultrathin membrane comprises a gas permeable, stretchable material having the thickness of less than about 300 microns and a total area of up to about 4 square inches which is used to hold the electronic components in place when they are applied to the skin of the user.

14. The system of claim 12 wherein the membrane has mounted thereon electronic components capable of detecting vibration of soft tissue associated with snoring.

* * * * *